US012650395B2

(12) United States Patent
Akimoto et al.

(10) Patent No.: US 12,650,395 B2
(45) Date of Patent: Jun. 9, 2026

(54) SENSOR AND SENSOR SYSTEM

(71) Applicant: KABUSHIKI KAISHA TOSHIBA, Tokyo (JP)

(72) Inventors: Yosuke Akimoto, Yokohama Kanagawa (JP); Hiroaki Yamazaki, Yokohama Kanagawa (JP)

(73) Assignee: KABUSHIKI KAISHA TOSHIBA, Kawasaki Kanagawa (JP)

( * ) Notice: Subject to any disclaimer, the term of this patent is extended or adjusted under 35 U.S.C. 154(b) by 378 days.

(21) Appl. No.: 18/353,297

(22) Filed: Jul. 17, 2023

(65) Prior Publication Data

US 2024/0201114 A1 Jun. 20, 2024

(30) Foreign Application Priority Data

Dec. 14, 2022 (JP) ................................. 2022-199696

(51) Int. Cl.
  *G01N 25/18* (2006.01)
  *G01N 33/00* (2006.01)
(52) U.S. Cl.
  CPC ......... *G01N 25/18* (2013.01); *G01N 33/0032* (2013.01); *G01N 33/0062* (2013.01)
(58) Field of Classification Search
  CPC .............. G01N 25/18; G01N 33/0009; G01N 33/0027; G01N 33/0031; G01N 33/0032; G01N 33/0036; G01N 33/0062; G01L 13/025; G01L 19/147; B81B 3/0097; B81B 2201/02; B81B 2203/0127
  See application file for complete search history.

(56) References Cited

U.S. PATENT DOCUMENTS

2012/0206147 A1*  8/2012  Sim ........................... G01K 7/34
                                                       324/457
2019/0086377 A1*  3/2019  Ikehashi .............. G01N 27/221

FOREIGN PATENT DOCUMENTS

CN      113790833 A    12/2021
JP      2011-85505 A    4/2011
JP      2015-132591 A   7/2015
JP      2017-36935 A    2/2017

OTHER PUBLICATIONS

Japan Patent Office, Office Action in JP App. No. 2022-199696 (Nov. 17, 2025).

* cited by examiner

*Primary Examiner* — Benjamin R Schmitt
(74) *Attorney, Agent, or Firm* — Finnegan, Henderson, Farabow, Garrett & Dunner, LLP

(57) ABSTRACT

A sensor includes a base including a first region and a second region; and a first sensor section. The first sensor section includes a first support portion fixed to the first region, a first structure, and a first film portion. The first structure is supported by the first support portion. The first structure includes a first resistance member. A first direction from the second region to the first structure crosses a second direction from the first region to the second region. The first film portion is fixed to the first region. A first gap is provided between the second region and the first film portion. A second gap is provided between the first film portion and the first structure.

18 Claims, 13 Drawing Sheets

SENSOR AND SENSOR SYSTEM

CROSS-REFERENCE TO RELATED APPLICATIONS

This application is based upon and claims the benefit of priority from Japanese Patent Application No. 2022-199696, filed on Dec. 14, 2022; the entire contents of which are incorporated herein by reference.

FIELD

Embodiments described herein relate generally to a sensor and a sensor system.

BACKGROUND

For example, there is a thermal conduction type gas sensor having a MEMS (Micro Electro Mechanical Systems) structure. It is desired to improve the accuracy of the sensor.

DETAILED DESCRIPTION

Figure 1:
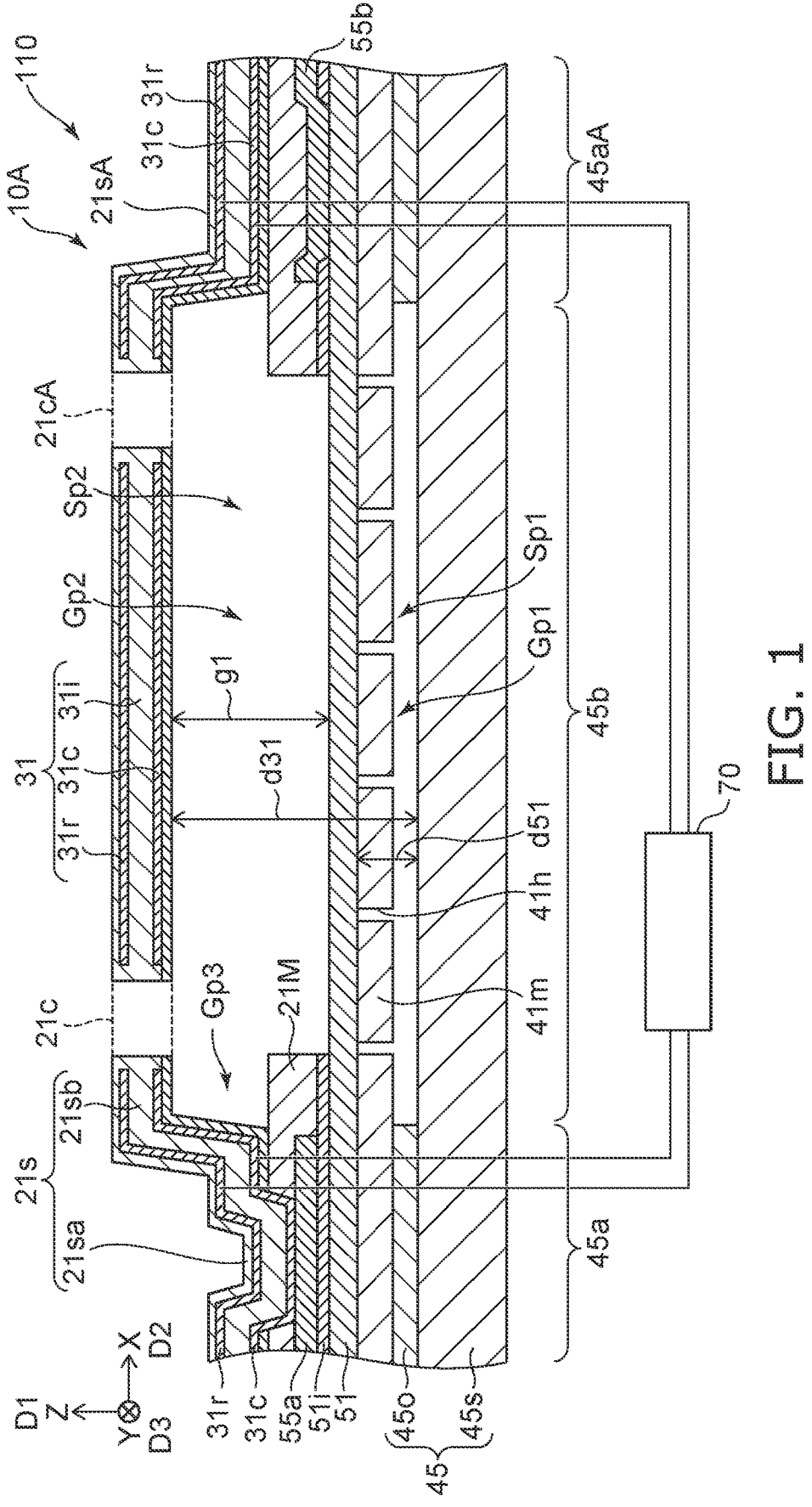
FIG. 1 is a schematic cross-sectional view illustrating a sensor according to a first embodiment.

According to one embodiment, a sensor includes a base including a first region and a second region; and a first sensor section. The first sensor section includes a first support portion fixed to the first region, a first structure, and a first film portion. The first structure is supported by the first support portion. The first structure includes a first resistance member. A first direction from the second region to the first structure crosses a second direction from the first region to the second region. The first film portion is fixed to the first region. A first gap is provided between the second region and the first film portion. A second gap is provided between the first film portion and the first structure.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic cross-sectional view illustrating a sensor according to a first embodiment.

Figure 2:
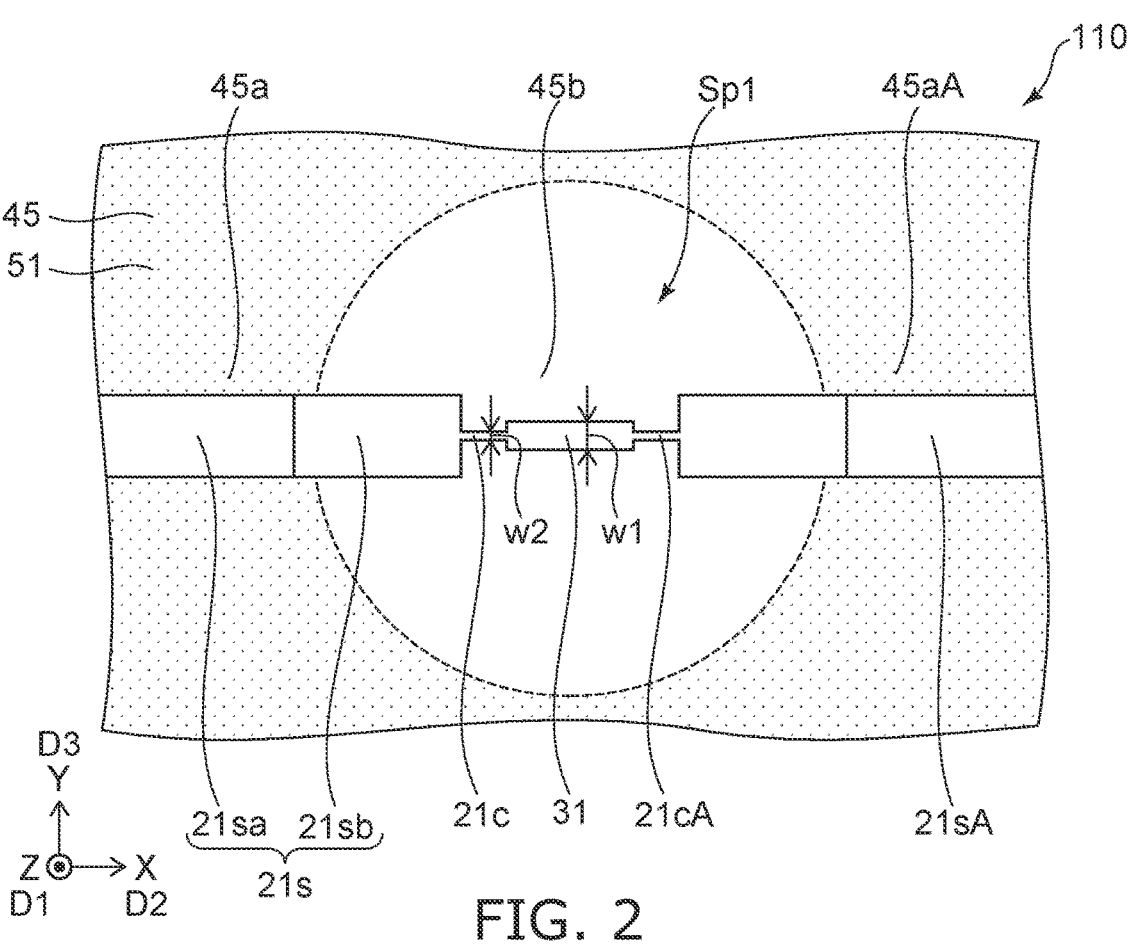
FIG. 2 is a schematic plan view illustrating the sensor according to the first embodiment.

FIG. 2 is a schematic plan view illustrating the sensor according to the first embodiment.

As shown in FIGS. 1 and 2, a sensor 110 according to the embodiment includes a base 45 and a first sensor section 10A.

The base 45 includes a first region 45a and a second region 45b.

The first sensor section 10A includes a first support portion 21s, a first structure 31 and a first film portion 51. The first support portion 21s is fixed to the first region 45a. The first structure 31 includes a first resistance member 31r. The first structure 31 is supported by the first support portion 21s. A first direction D1 from the second region 45b to the first structure 31 crosses a second direction D2 from the first region 45a to the second region 45b. For example, the first structure 31 is a membrane.

The first direction D1 is defined as a Z-axis direction. One direction perpendicular to the Z-axis direction is defined as an X-axis direction. A direction perpendicular to the Z-axis direction and the X-axis direction is defined as a Y-axis direction. The first direction D1 is, for example, perpendicular to the upper surface of the base 45.

In this example, the first structure 31 further includes a first conductive member 31c and a first insulating member 31i. At least a part of the first insulating member 31i is provided around the first resistance member 31r. A part of the first insulating member 31i is provided around the first conductive member 31c. The first conductive member 31c may function, for example, as a heater.

The first film portion 51 is fixed to the first region 45a. A first gap Gp1 is provided between the second region 45b and the first film portion 51. A second gap Gp2 is provided between the first film portion 51 and the first structure 31. The first film portion 51 is, for example, a diaphragm.

The first electrical resistance of the first resistance member 31r included in the first structure 31 changes according to the temperature of the first structure 31. The temperature of the first structure 31 can change according to the detection target gas around the first structure 31.

For example, current is supplied to the first conductive member 31c, and Joule heat causes the temperature of the first conductive member 31c to rise, and the temperature of the first structure 31 to rise. The heat of the first structure 31 is dissipated to the space around the first structure 31. For example, the degree of heat dissipation changes depending on the detection target gas that exists around the first structure 31. The degree of decrease in the temperature of the first structure 31 is related to the detection target gas. By detecting a change in the temperature of the first structure 31, the detection target gas can be detected. Thus, the first electrical resistance changes according to the detection target gas around the first structure 31. The sensor is, for example, a thermal conductivity gas sensor.

The detection target gas to may include, for example, at least one selected from the group consisting of hydrogen, carbon dioxide, methane, ammonia, helium, and water vapor.

The temperature (and change in temperature) of the first conductive member 31c may be detected by a controller 70 (see FIG. 1). The power supply to the first conductive member 31c may be controlled by the controller 70 (see FIG. 1).

For example, the controller 70 is configured to increase the temperature of the first structure 31 by supplying power to the first conductive member 31c. The controller 70 is configured to detect the change in the first electrical resistance of the first resistance member 31r according to a change in temperature of the first structure 31.

The heat dissipation from the first structure 31 is affected by the pressure of the second space Sp2 between the first structure 31 and the first film portion 51. For example, even if the type and concentration of the detection target gas passing through the second space Sp2 are constant, the degree of heat dissipation from the first structure 31 changes when the pressure in the second space Sp2 changes.

As described above, the first sensor section 10A includes the first film portion 51 in the embodiment. The central portion of the first film portion 51 can be displaced according to the pressure of the second space Sp2. Due to the displacement of the central portion of the first film portion 51, the output change caused by the pressure change in the second space Sp2 can be alleviated. As a result, high detection accuracy can be maintained even when the pressure of the detection target gas changes. According to the embodiment, it is possible to provide a sensor capable of improving accuracy.

For example, the thermal resistance Rx between the first film portion 51 and the first structure 31 is represented by the following formula (1).

$$Rx = g1/(\rho a \times S1) \tag{1}$$

In the formula (1), "g1" is the distance between the first film portion 51 and the first structure 31 (see FIG. 1). "ρa" is the thermal conductivity in the second space Sp2. "S1" is the area of the first structure 31.

In the embodiment, the first film portion 51 is provided. As the pressure in the second space Sp2 increases, the thermal conductivity ρa increases. On the other hand, when the pressure in the second space Sp2 increases, the central portion of the first film portion 51 is displaced closer to the base 45, increasing the distance g1. Since the thermal conductivity ρa increases and the distance g1 increases, the change in the thermal resistance Rx is moderated according to the formula (1).

On the other hand, when the pressure in the second space Sp2 decreases, the thermal conductivity ρa decreases. On the other hand, when the pressure in the second space Sp2 decreases, the central portion of the first film portion 51 is displaced away from the base 45, and the distance g1 decreases. Since the thermal conductivity ρa decreases and the distance g1 decreases, the change in the thermal resistance Rx is moderated according to the formula (1). High detection accuracy can be maintained even when the pressure of the detection target gas changes.

Preferably, a first pressure in the first space Sp1 (see FIG. 1) between the second region 45b and the first film portion 51 is lower than a second pressure in the second space Sp2 between the first film portion 51 and the first structure 31. Thereby, heat dissipation through the first space Sp1 is suppressed. Thus, for example, the temperature of the first structure 31 responds substantially depending only on the thermal resistance variation of the first space Sp1. Thereby, detection with higher accuracy is possible. The pressure of the second space Sp2 may be, for example, atmospheric pressure. The pressure in the second space Sp2 may change depending on the pressure of the introduced detection target gas. The first space Sp1 is decompressed, for example. The pressure in the first space Sp1 is equal to or less than atmospheric pressure.

As shown in FIG. 1, as described above, the distance along the Z-axis direction between the second region 45b and the first film portion 51 is defined as the first film portion distance d51. The first film portion distance d51 is configured to be changed according to the pressure of the second space Sp2.

As shown in FIG. 1, the distance along the Z-axis direction between the second region 45b and the first structure 31 is defined as a first structure distance d31. The first structure distance d31 does not substantially change. Alternatively, the change in the first structure distance d31 is smaller than the change in the first film portion distance d51.

For example, the pressure of the second space Sp2 in a first state is higher than the pressure of the second space Sp2 in a second state. The first film portion distance d51 in the first state (high pressure) is shorter than the first film portion distance d51 in the second state (low pressure). The distance g1 between the first film portion 51 and the first structure 31 in the first state is longer than the distance g1 between the first film portion 51 and the first structure 31 in the second state. High accuracy results are obtained in which pressure changes are compensated. For example, the first film portion distance d51 in the first state is shorter than the first film portion distance d51 in the second state. The distance g1 between the first film portion 51 and the first structure 31 in the first state is longer than the distance g1 between the first film portion 51 and the first structure 31 in the second state. For example, the conduction of heat from the first structure 31 to the first film portion 51 decreases in response to an increase in the distance g1 between the first film portion 51 and the first structure 31. The displacement of the first film portion 51 in response to the pressure compensates for heat conduction.

The first space Sp1 may be sealed by the second region 45b and the first film portion 51. As shown in FIG. 1, the first sensor section 10A may further include a first intermediate film 41m. The first intermediate film 41m is provided between the second region 45b and the first film portion 51. The first intermediate film 41m is fixed to the first film portion 51. The first intermediate film 41m includes a first hole 41h. The first hole 41h pierces the first intermediate film 41m in the first direction D1. A first gap Gp1 is provided between the second region 45b and the first intermediate film 41m.

As shown in FIGS. 1 and 2, in this example, the first sensor section 10A further includes a first connect portion 21c. A part of the first connect portion 21c is connected to the first support portion 21s. Another part of the first connect portion 21c is connected to the first structure 31. A width w2 of the first connect portion 21c in a third direction D3 is narrower than a width w1 of the first structure 31 in the third direction D3. The third direction D3 crosses a plane including the first direction D1 and the second direction D2. The third direction D3 is, for example, the Y-axis direction. By the width w2 being narrow, heat conduction via the first connect portion 21c is suppressed. Thereby, the first structure 31 can be heated with low power consumption.

As shown in FIGS. 1 and 2, the first sensor section 10A may further include a first opposing support portion 21sA. The base 45 further includes a first facing region 45aA. In the second direction D2, the second region 45b is provided between the first region 45a and the first opposing region 45aA. The first opposing support portion 21sA is fixed to the first opposing region 45aA. A part of the first structure 31 is supported by the first opposing support portion 21sA. In this example, the first sensor section 10A includes a first opposing connect portion 21cA. The first structure 31 is supported by the first opposing support portion 21sA via the first opposing connect portion 21cA.

The configuration of the first opposing support portion 21sA may be the same as the configuration of the first support portion 21s. The configuration of the first opposing connect portion 21cA may be the same as the configuration of the first connect portion 21c.

The first resistance member 31r may pass through the first support portion 21s and the first opposing support portion 21sA. The first conductive member 31c may pass through the first support portion 21s and the first opposing support portion 21sA.

As shown in FIG. 1, for example, the first support portion 21s may include a first support part 21sa and a second support part 21sb. The first support part 21sa is fixed to the first region 45a. The second support part 21sb is continuous with the first support part 21sa. A third gap Gp3 is provided between the first film portion 51 and the second support part 21sb.

As shown in FIG. 1, the first sensor section 10A may further include a first fixing member 21M. The first fixing member 21M is provided between a part of the first film portion 51 and the second support part 21sb. The first fixing member 21M is fixed to the first film portion 51. The third gap Gp3 is provided between the first fixing member 21M and the second support part 21sb. By adjusting the position along the X-axis direction of the end of the first fixing member 21M, the ease of displacement (hardness) of the central portion of the first film portion 51 can be adjusted. The first fixing member 21M includes, for example, silicon nitride.

In FIG. 1, the base 45 may include a substrate 45s and an insulating layer 45o. The substrate 45s may be, for example, a silicon substrate. The insulating layer 45o may include, for example, silicon oxide. The insulating layer 45o is, for example, a BOX (Buried Oxide) layer. The thickness of the insulating layer 45o is, for example, 5 μm (e.g., not less than 3 μm and not more than 7 μm).

In the first region 45a, the insulating layer 45o is provided between the substrate 45s and the first support portion 21s. A part where the insulating layer 45o is not provided corresponds to the first gap Gp1 (first space Sp1).

The first intermediate film 41m is provided between the insulating layer 45o and the first support portion 21s. The first intermediate film 41m includes Si, for example. The thickness of the first intermediate film 41m is, for example, 5 μm (e.g., not less than 3 μm and not more than 7 μm).

A part (for example, the outer edge) of the first film portion 51 is provided between the first intermediate film 41m and the first support portion 21s. A first electrode layer 55a may be provided between a part of the first film portion 51 and the first support portion 21s. The first electrode layer 55a is electrically connected to, for example, the first conductive member 31c. The first electrode layer 55a includes Al, for example. The thickness of the first electrode layer 55a is, for example, 0.6 μm (e.g., not less than 0.4 μm and not more than 0.8 μm).

As shown in FIG. 1, a second electrode layer 55b may be provided. The second electrode layer 55b is electrically connected to the first film portion 51.

As shown in FIG. 1, an insulating film 51i is provided between the first film portion 51 and the first electrode layer 55a. The insulating film 51i includes, for example, silicon nitride. The thickness of the insulating film 51i is, for example, 0.3 μm (e.g., not less than 0.1 μm and not more than 0.5 μm).

In one example, the first film portion 51 includes polysilicon, for example. In this case, the first film portion 51 is conductive. In this case, at least a part of the base 45 (e.g., the second region 45b) may be conductive. As will be described below, the capacitance between the base 45 and the first film portion 51 may be detected. The first film portion 51 may be insulative.

The first resistance member 31r includes TIN, for example. The thickness of the first resistance member 31r is, for example, 0.1 μm (e.g., not less than 0.06 μm and not more than 0.14 μm). The first conductive member 31c includes TiN, for example. The thickness of the first conductive member 31c is, for example, 0.1 μm (e.g., not less than 0.06 μm and not more than 0.14 μm). The first insulating member 31i includes, for example, silicon and oxygen. The first insulating member 31i includes silicon nitride, for example.

An example of a method for manufacturing the sensor 110 will be described below.

FIG. 3 to FIG. 5 and FIG. 8 to FIG. 15 are schematic cross-sectional views illustrating the method of manufacturing the sensor according to the first embodiment.

Figure 6:
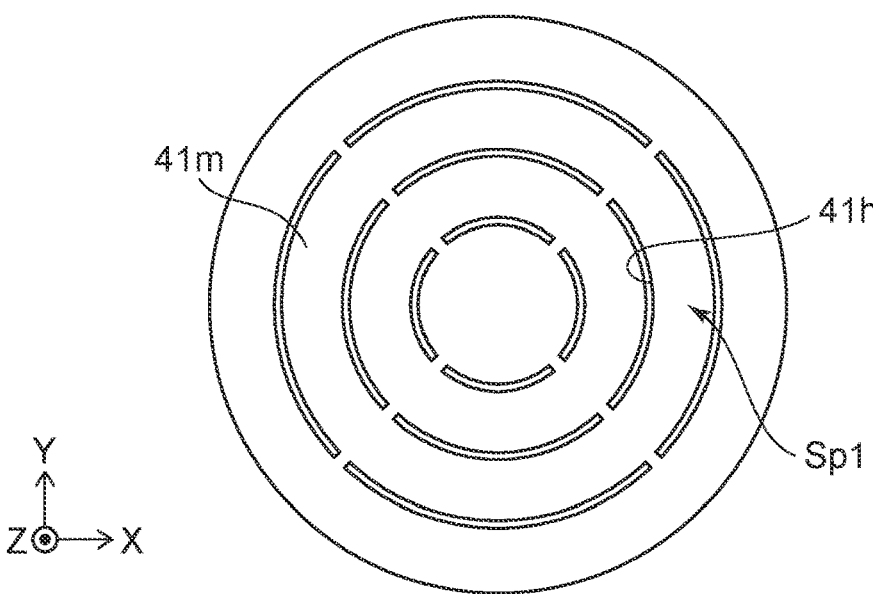
FIG. 6 is a schematic plan view illustrating the method for manufacturing the sensor according to the first embodiment.
Figure 7:
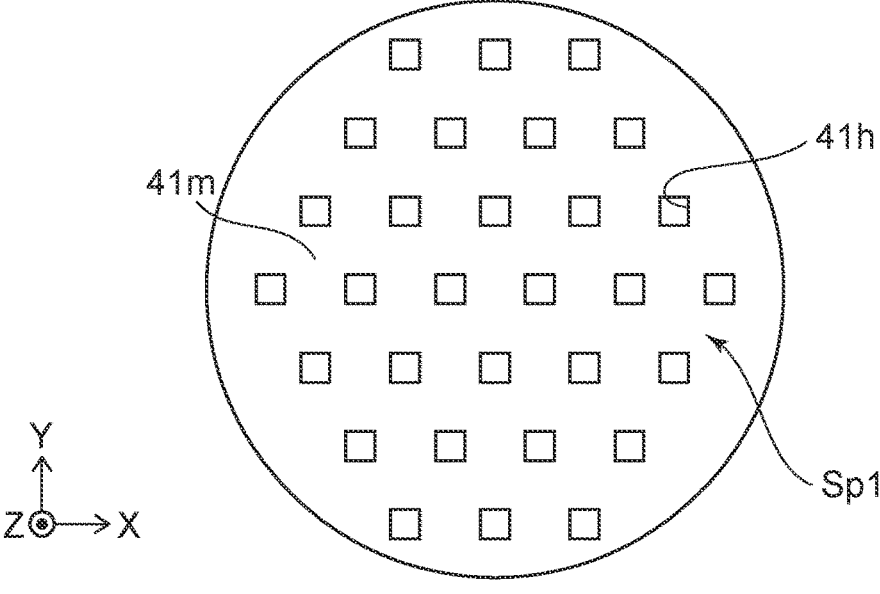
FIG. 7 is a schematic plan view illustrating the method for manufacturing the sensor according to the first embodiment.

FIG. 6 and FIG. 7 are schematic plan views illustrating the method for manufacturing the sensor according to the first embodiment.

Figure 3:
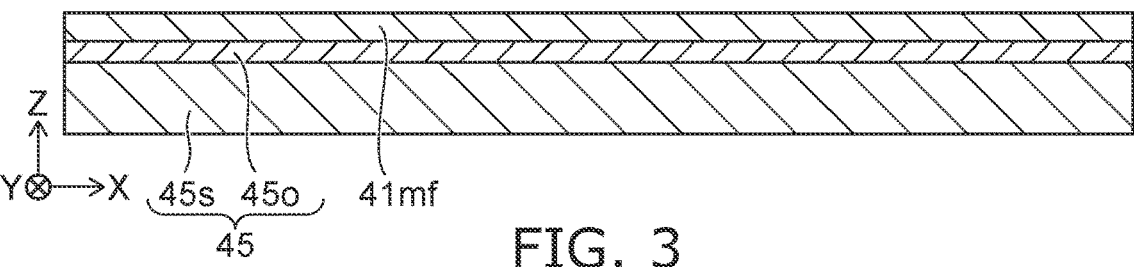
FIG. 3 is a schematic cross-sectional view illustrating a method of manufacturing the sensor according to the first embodiment.

As shown in FIG. 3, the base 45 includes the substrate 45*s* and the insulating layer 45*o*. A silicon film 41*mf* is provided on the insulating layer 45*o*.

Figure 4:
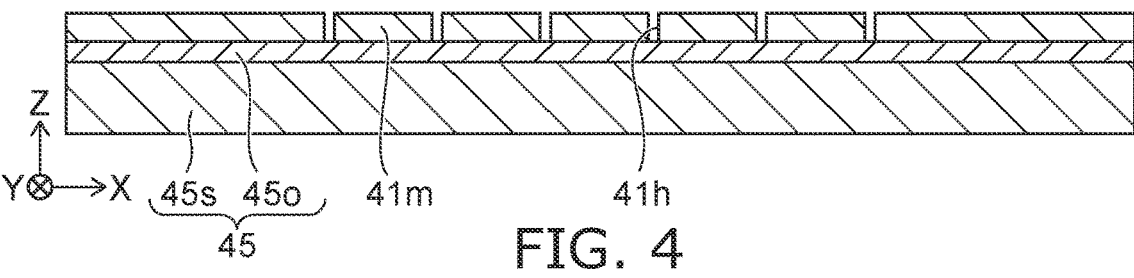
FIG. 4 is a schematic cross-sectional view illustrating the method of manufacturing the sensor according to the first embodiment.

As shown in FIG. 4, the first hole 41*h* is formed by removing a part of the silicon film 41*mf*. The first intermediate film 41*m* is obtained from the silicon film 41*mf*. The formation of the first hole 41*h* can be performed, for example, by RIE (Reactive Ion Etching).

Figure 5:
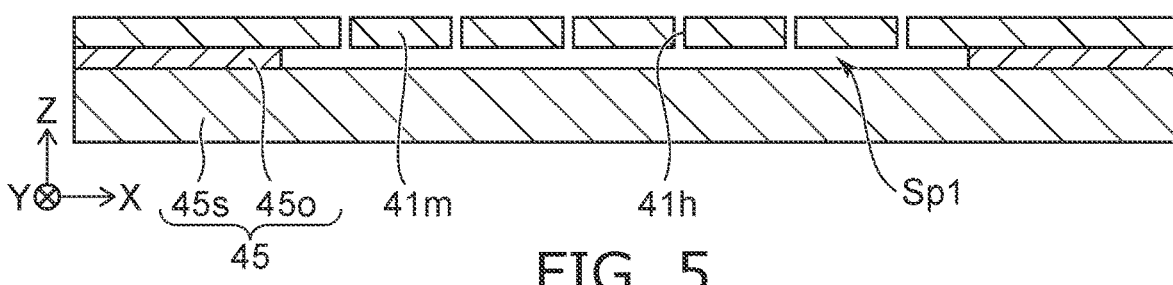
FIG. 5 is a schematic cross-sectional view illustrating the method of manufacturing the sensor according to the first embodiment.

As shown in FIG. 5, a part of the insulating layer 45*o* is removed through the first hole 41*h*. Thereby, the first space Sp1 is formed. For example, the removal of the part of the insulating layer 45*o* can be performed by hydrofluoric acid treatment.

FIG. 6 and FIG. 7 illustrate patterns of the first holes 41*h* and the first spaces Sp1. The shape and arrangement of the first hole 41*h* are arbitrary. In this example, the pattern of the first space Sp1 is circular. As will be described below, various modifications of the pattern are possible.

Figures 8, 9, 10:
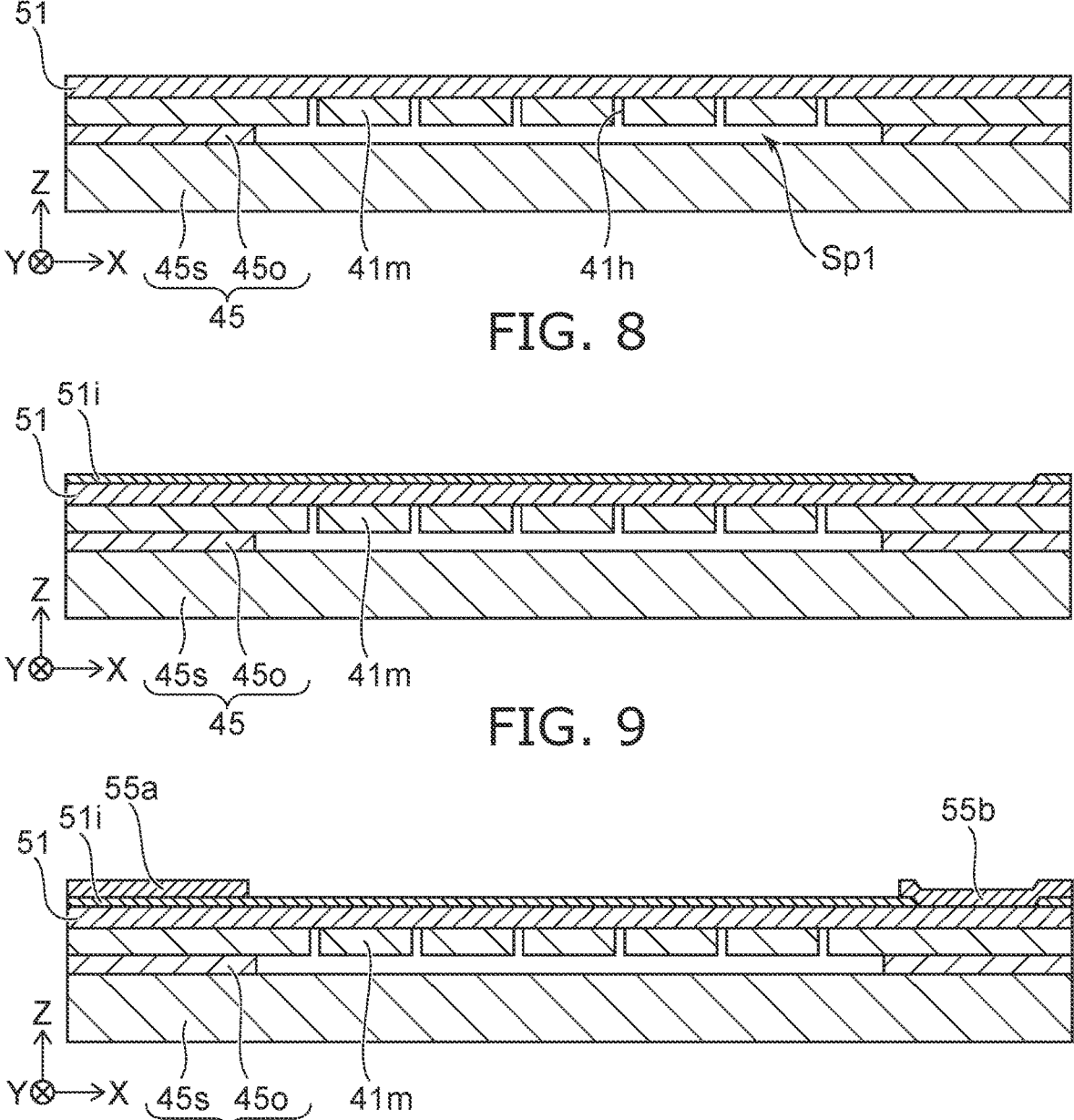
FIG. 8 is a schematic cross-sectional view illustrating the method of manufacturing the sensor according to the first embodiment.
FIG. 9 is a schematic cross-sectional view illustrating the method of manufacturing the sensor according to the first embodiment.
FIG. 10 is a schematic cross-sectional view illustrating the method of manufacturing the sensor according to the first embodiment.

As shown in FIG. 8, the first film portion 51 (e.g., polysilicon film) is formed. The formation of the polysilicon film can be performed, for example, by CVD (Chemical Vapor Deposition).

As shown in FIG. 9, the insulating film 51*i* (for example, a silicon nitride film) is formed, and if necessary, a part of the insulating film 51*i* is removed. Thereby, the contact portion is appropriately formed.

Figure 11:
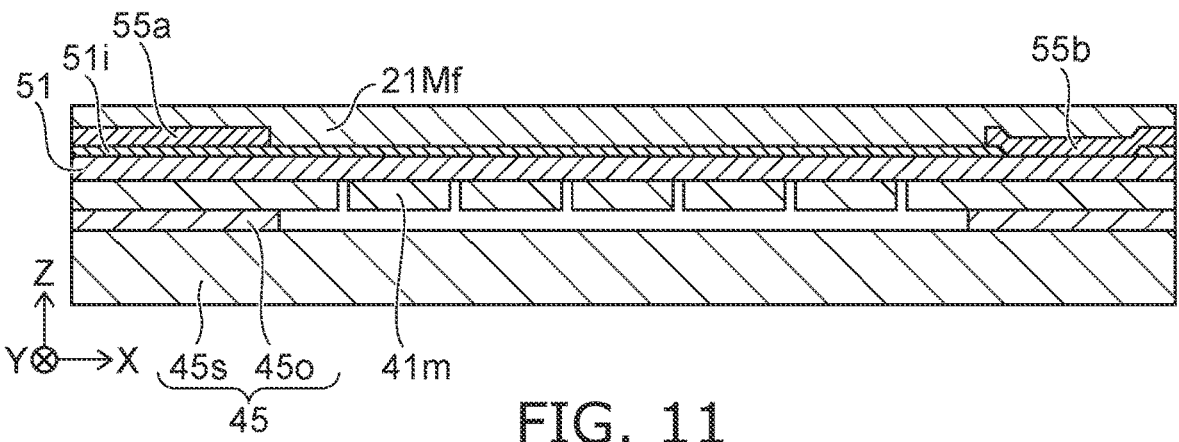
FIG. 11 is a schematic cross-sectional view illustrating the method of manufacturing the sensor according to the first embodiment.

As shown in FIG. 10, the first electrode layer 55*a* and the second electrode layer 55*b* are formed. As shown in FIG. 11, a silicon nitride film 21Mf serving as the first fixing member 21M is formed.

Figure 12:
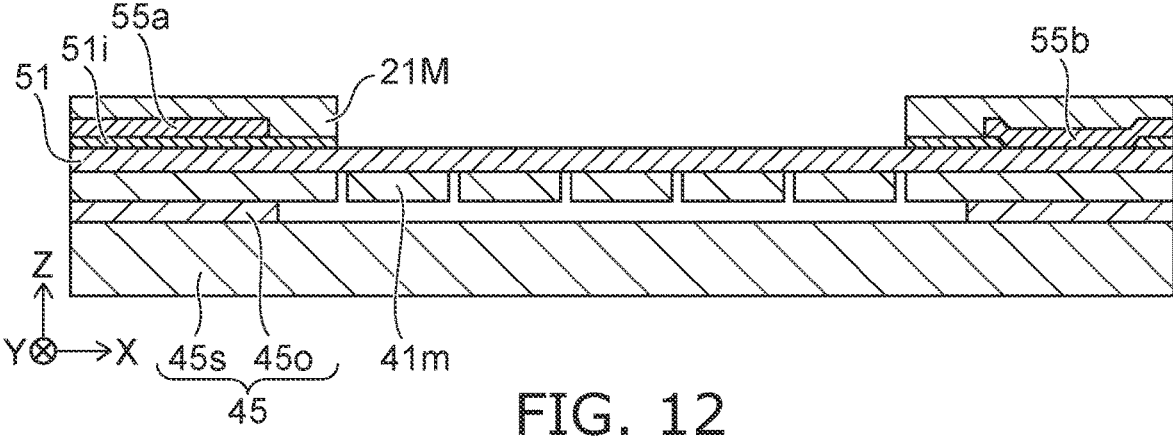
FIG. 12 is a schematic cross-sectional view illustrating the method of manufacturing the sensor according to the first embodiment.

As shown in FIG. 12, a part of the silicon nitride film 21Mf is removed. Thereby, the first fixing member 21M is obtained.

Figure 13:
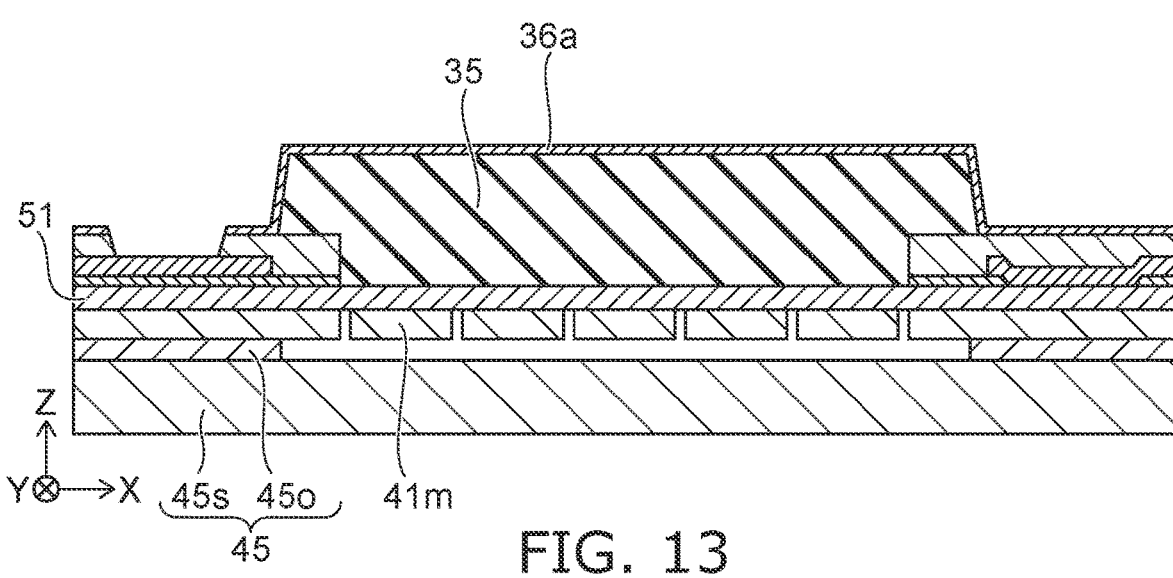
FIG. 13 is a schematic cross-sectional view illustrating the method of manufacturing the sensor according to the first embodiment.

As shown in FIG. 13, a sacrificial layer 35 having a predetermined pattern is formed, and a silicon nitride film 36*a* is formed. The sacrificial layer 35 may be, for example, polyimide. The thickness of the sacrificial layer 35 is, for example, approximately 2 μm.

Figure 14:
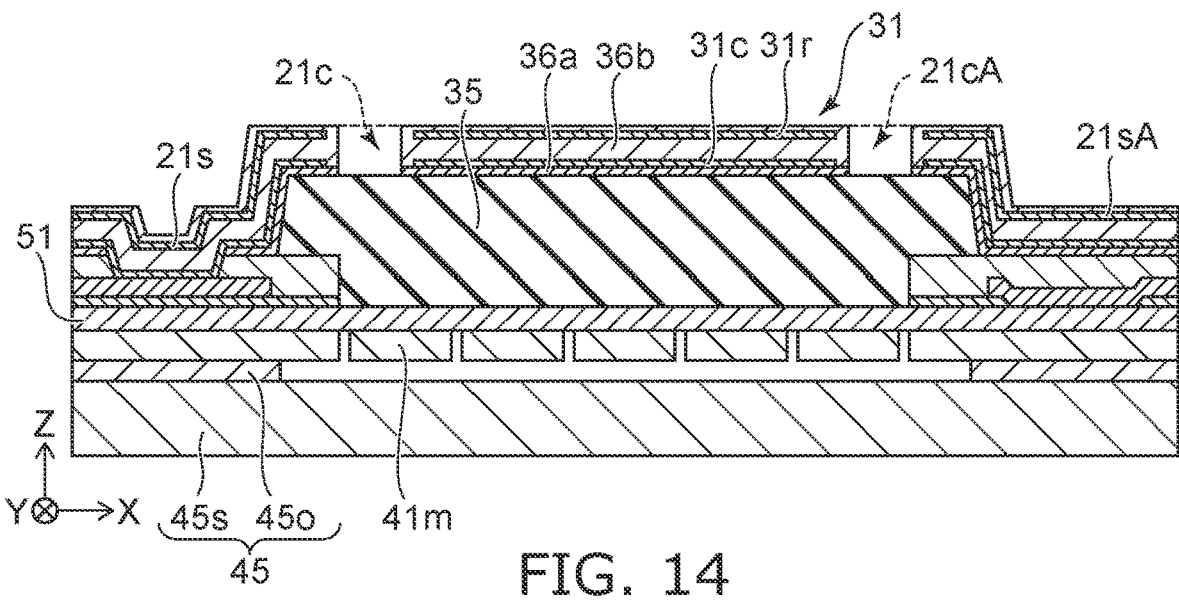
FIG. 14 is a schematic cross-sectional view illustrating the method of manufacturing the sensor according to the first embodiment.

As shown in FIG. 14, the first conductive member 31*c* (for example, TiN), a silicon nitride film 36*b* and the first resistance member 31*r* are formed in this order and processed into a predetermined shape. Thereby, the first structure 31, the first support portion 21*s*, the first connect portion 21*c*, the first opposing connect portion 21*c*A, and the first opposing support portion 21*s*A are formed.

Figure 15:
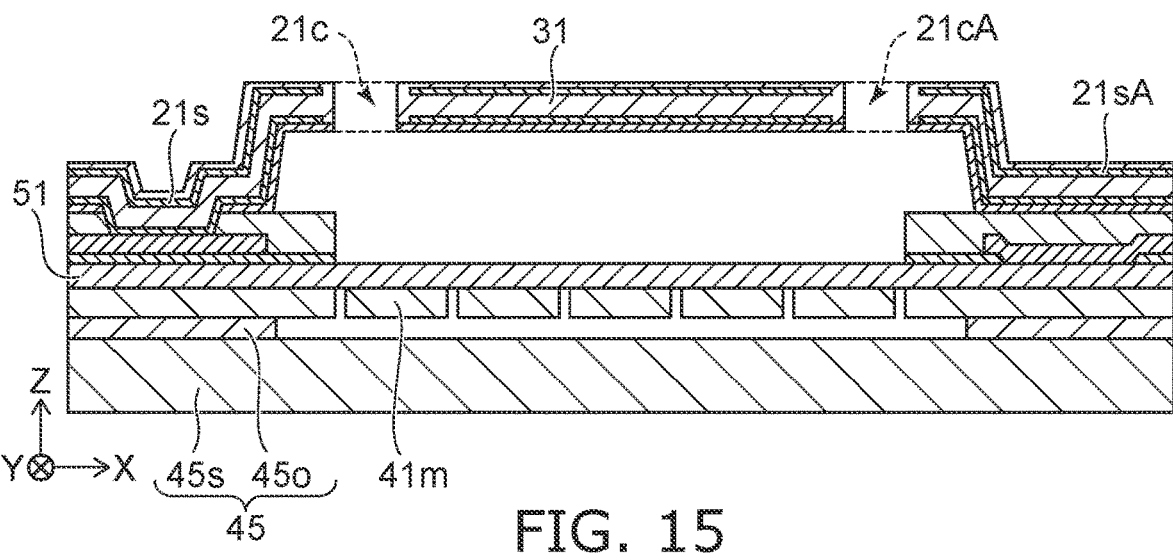
FIG. 15 is a schematic cross-sectional view illustrating the method of manufacturing the sensor according to the first embodiment.

As shown in FIG. 15, the sacrificial layer 35 is removed. Thereby, the sensor 110 is obtained. The sacrificial layer 35 can be removed, for example, through openings around the first connect portion 21*c* and the first opposing connect portion 21*c*A.

Figure 16:
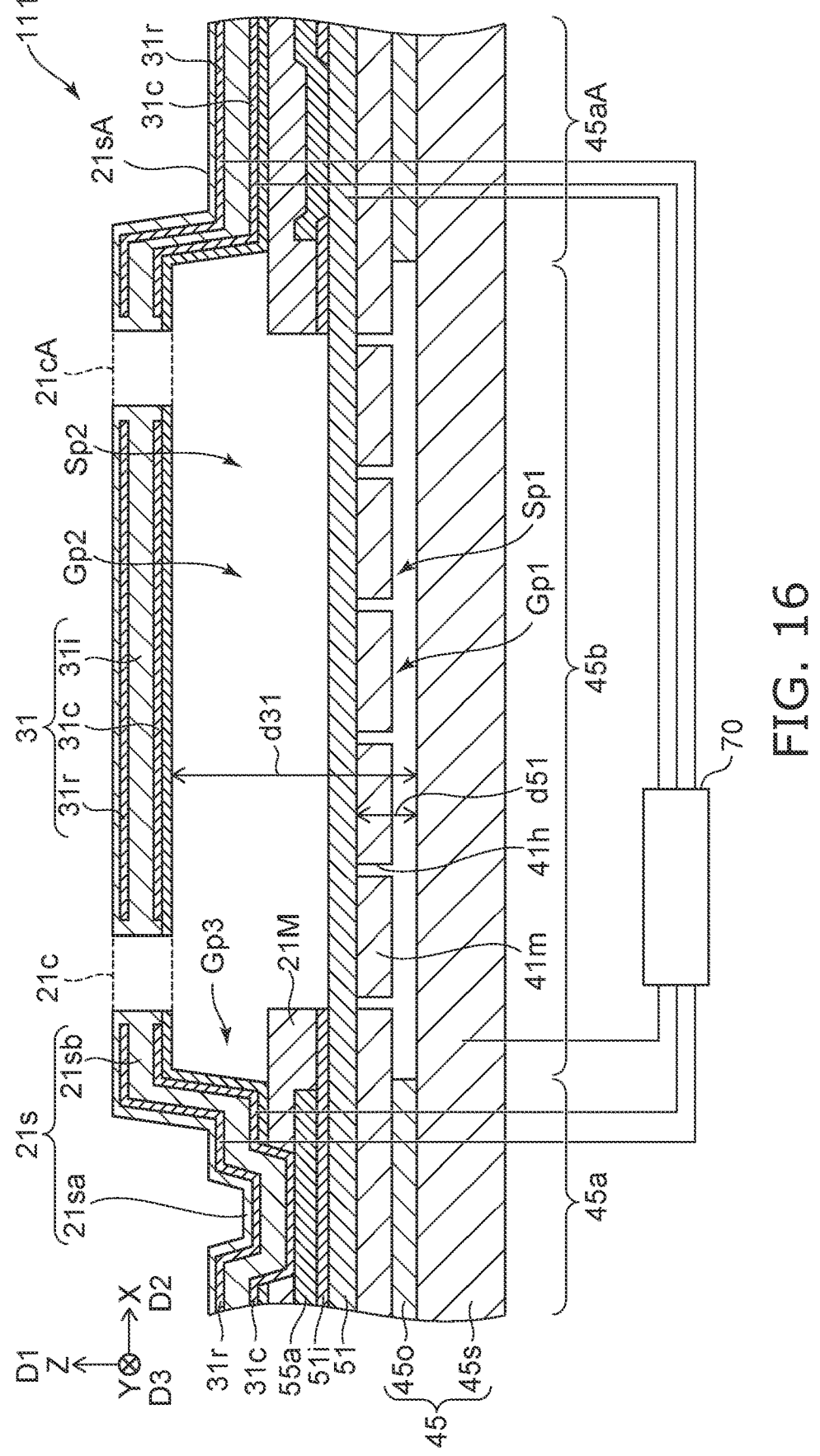
FIG. 16 is a schematic cross-sectional view illustrating a sensor according to the first embodiment.

FIG. 16 is a schematic cross-sectional view illustrating a sensor according to the first embodiment.

As shown in FIG. 16, in a sensor 111 according to the embodiment, the controller 70 is configured to detect a change in electric capacitance between the base 45 and the first film portion 51. The configuration of the sensor 111 excluding this may be the same as the configuration of the sensor 110.

In the sensor 111, the first film portion 51 is conductive and at least a part of the second region 45*b* is conductive. For example, the first film portion 51 includes polysilicon. The base 45 includes, for example, silicon.

In the sensor 111, the controller 70 may detect pressure based on the detection result of the change in the electric capacitance between the base 45 and the first film portion 51.

For example, the displacement of the first film portion 51 in response to the pressure can be detected by detecting the change in capacitance.

In the sensor 111, the controller 70 may correct the detection result of the change in the first electrical resistance based on the detection result of the change in electrical capacitance between the base 45 and the first film portion 51. Higher precision detection is possible.

Figure 17:
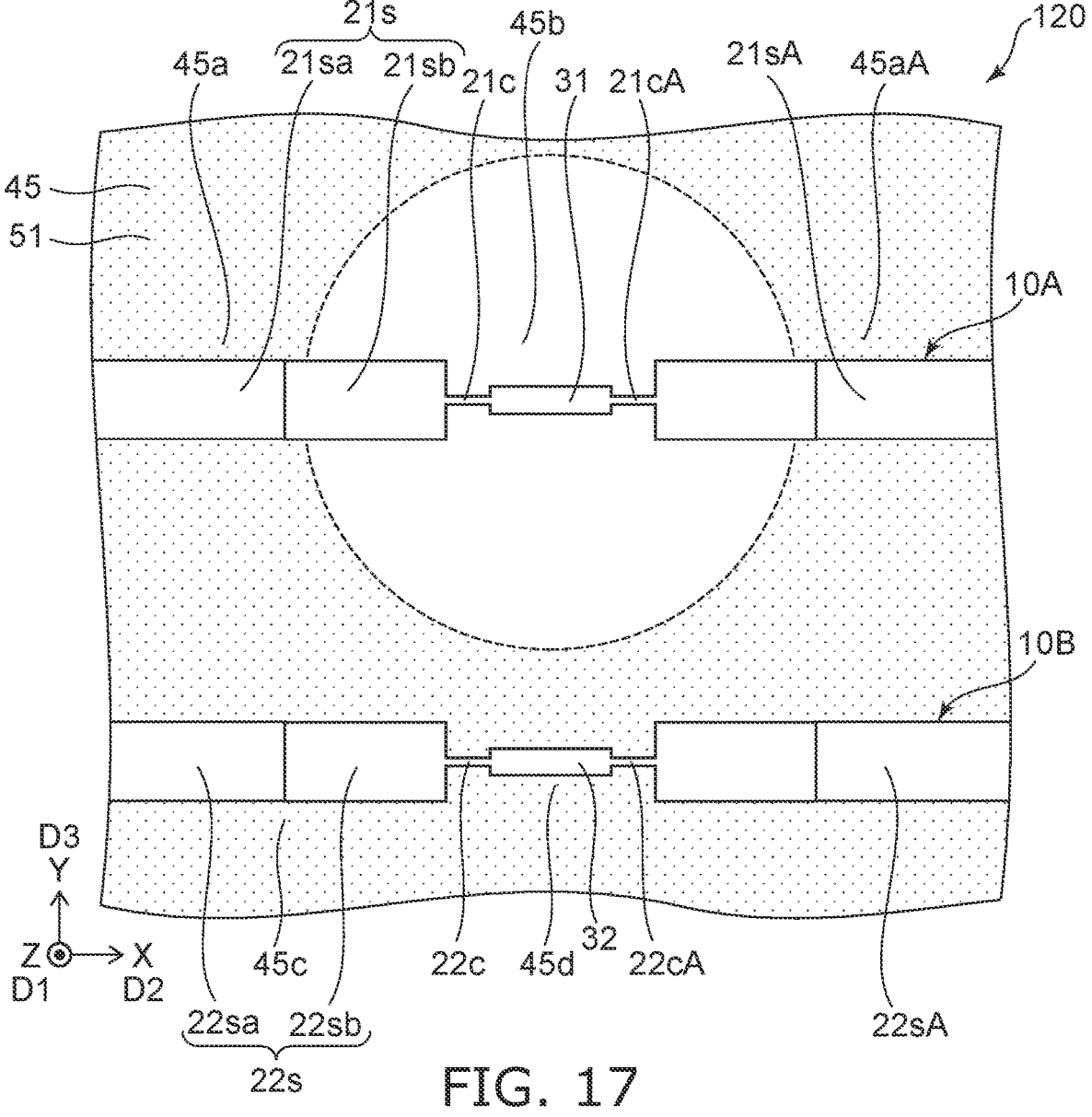
FIG. 17 is a schematic plan view illustrating a sensor according to the first embodiment.

FIG. 17 is a schematic plan view illustrating a sensor according to the first embodiment.

Figure 18:
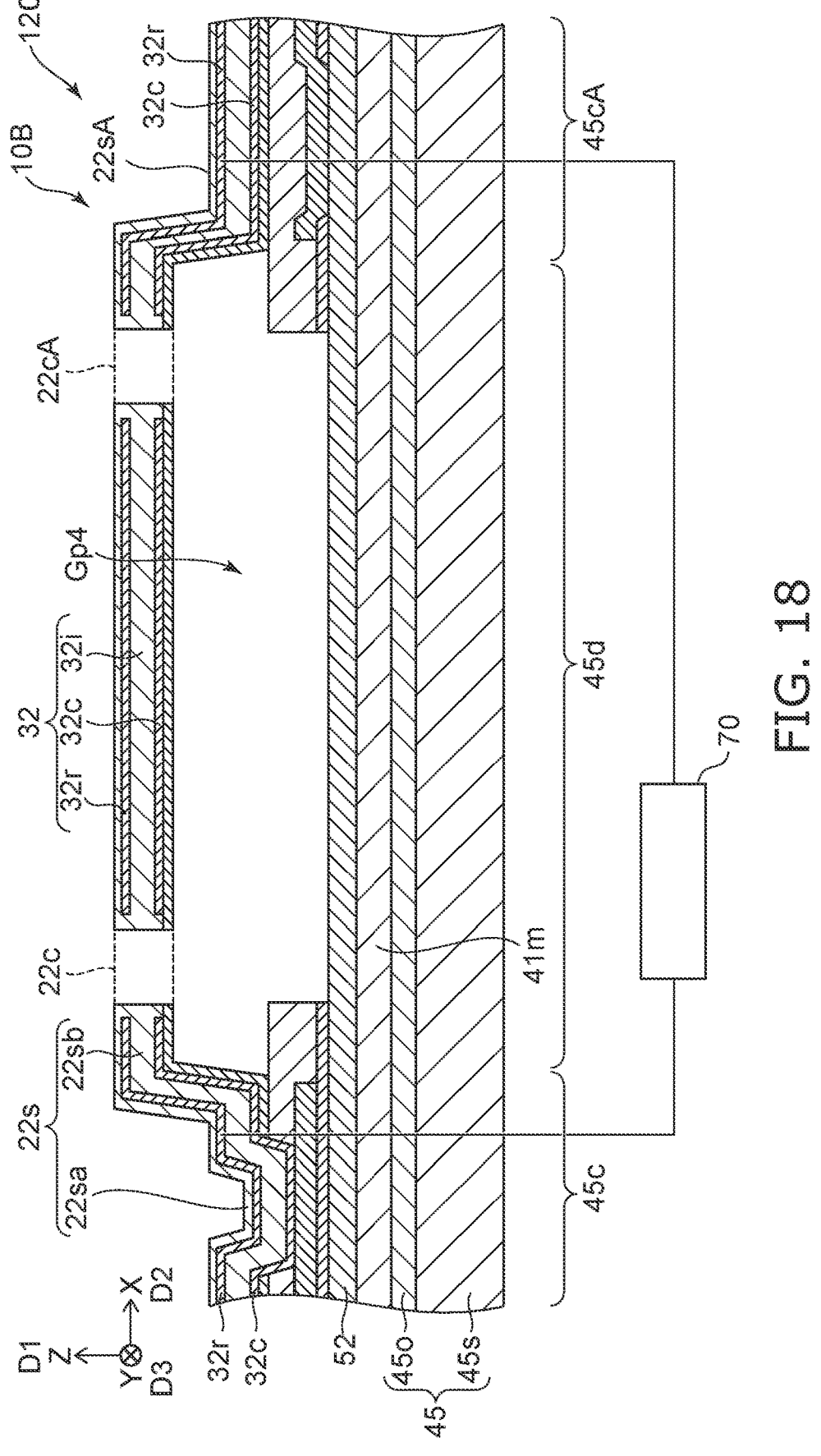
FIG. 18 is a schematic cross-sectional view illustrating the sensor according to the first embodiment.

FIG. 18 is a schematic cross-sectional view illustrating the sensor according to the first embodiment.

As shown in FIG. 17, a sensor 120 according to the embodiment further includes a second sensor section 10B in addition to the base 45 and the first sensor section 10A. The base 45 further includes a third region 45*c* and a fourth region 45*d*.

FIG. 18 illustrates the second sensor section 10B. As shown in FIG. 18, the second sensor section 10B includes a second support portion 22*s* and a second structure 32. The second support portion 22*s* is fixed to the third region 45*c*.

The second structure 32 includes a second resistance member 32*r*. The second structure 32 may include a second conductive member 32*c*. The second structure 32 is supported by the second support portion 22*s*. In this example, the second structure 32 is supported by the second support portion 22*s* via the second connect portion 22*c*. A direction from the fourth region 45*d* to the second structure 32 is along the first direction D1. A fourth gap Gp4 is provided between the fourth region 45*d* and the second structure 32. At least a part of a second insulating member 32*i* of the second structure 32 is provided around the second resistance member 32*r* and the second conductive member 32*c*.

As shown in FIG. 18, the second sensor section 10B includes a second film portion 52 in this example. The second film portion 52 is continuous with the first film portion 51. No gap is provided between the fourth region 45*d* of the base 45 and the second film portion 52.

The second sensor section 10B functions, for example, as a reference element. No power is supplied to the second conductive member 32*c* included in the second structure 32. The second structure 32 is not heated. The second conductive member 32*c* is, for example, a dummy heater. The second electrical resistance of the second resistance member 32*r* of the second structure 32 is substantially unaffected by the detection target gas. By calculating the difference between the second electric resistance and the first electric resistance, effects other than the detection target gas can be suppressed.

Thus, the controller 70 may correct the detection result of the change in the first electrical resistance of the first resistance member 31*r* based on the detection result of the second electrical resistance of the second resistance member 32*r*. The detection target gas can be detected with higher accuracy.

As shown in FIG. 17 and FIG. 18, the second sensor section 10B may include a second opposing connect portion 22*c*A and a second opposing support portion 22*s*A.

Figure 19:
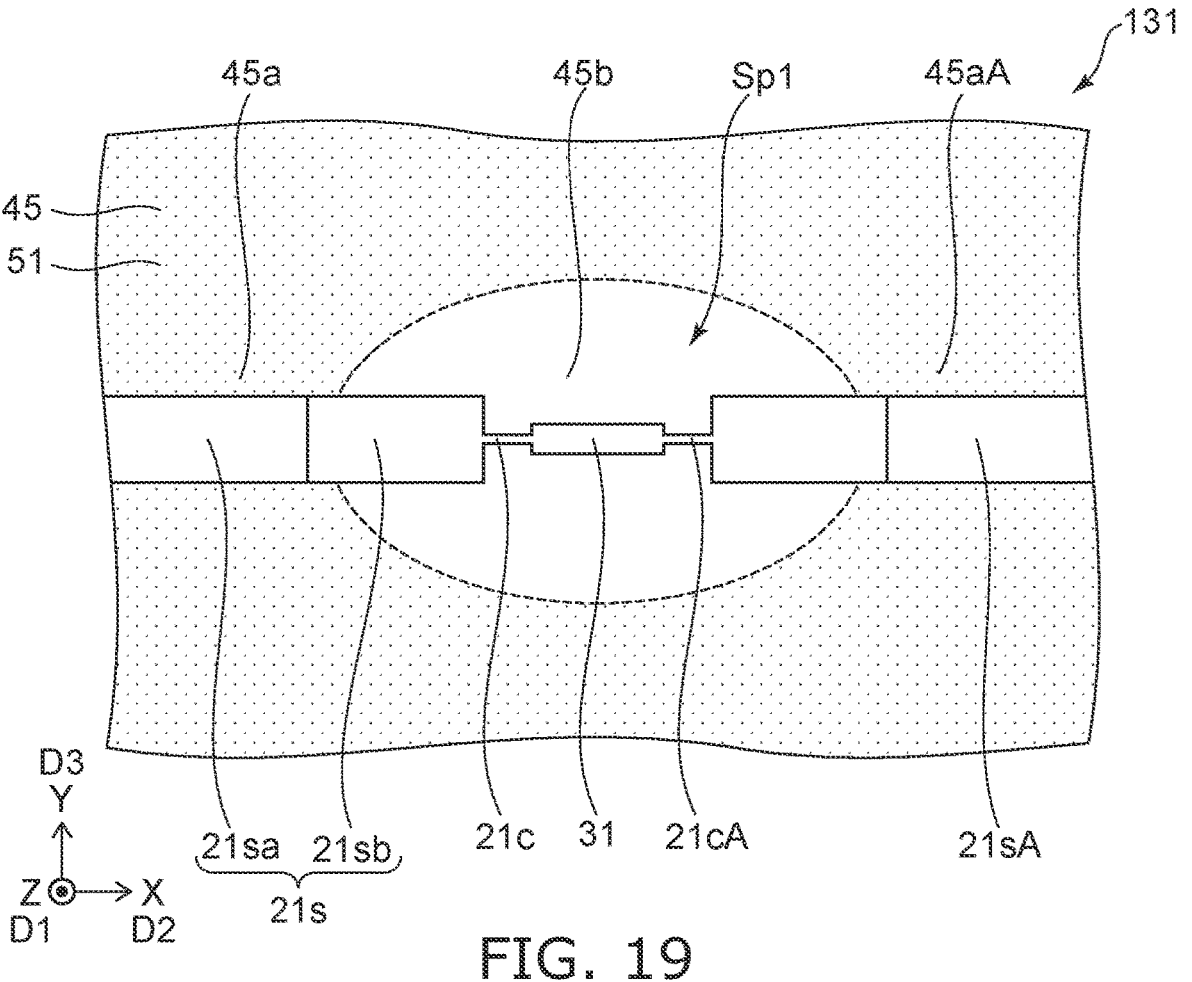
FIG. 19 is a schematic plan view illustrating a sensor according to the embodiment.
Figure 20:
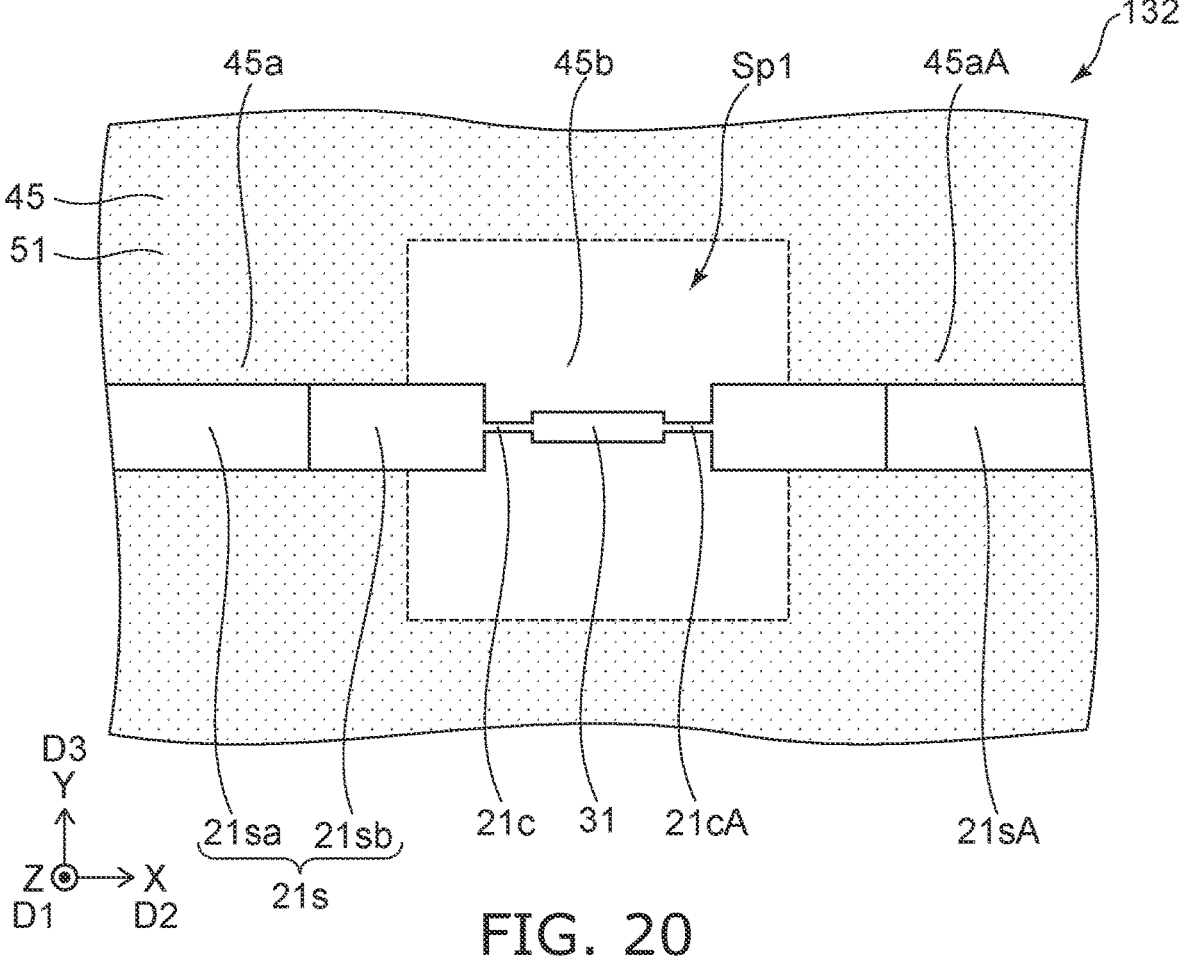
FIG. 20 is a schematic plan view illustrating a sensor according to the embodiment.

FIGS. 19 and 20 are schematic plan views illustrating a sensor according to the embodiment. As shown in FIG. 19, in a sensor 131 according to the embodiment, the planar shape of the first space Sp1 is a flat circle (including an ellipse). As shown in FIG. 20, in a sensor 132 according to the embodiment, the planar shape of the first space Sp1 is polygonal. The planar shape of the first space Sp1 may be a quadrangle. A number of corners in polygon may be arbitrary. The planar shape of the first space Sp1 is arbitrary.

Second Embodiment

Figure 21:
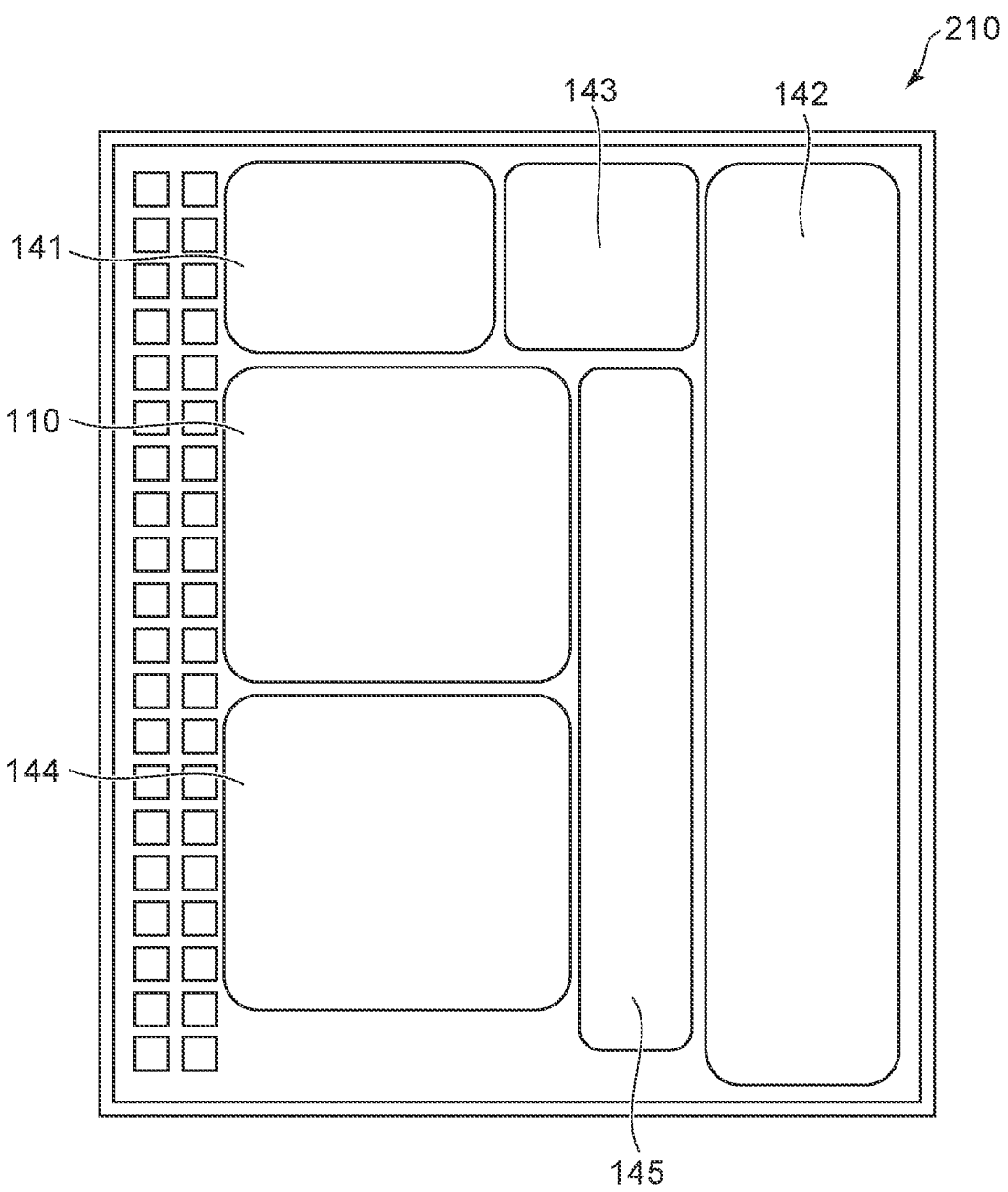
FIG. 21 is a schematic plan view illustrating a sensor system according to a second embodiment.

FIG. 21 is a schematic plan view illustrating a sensor system according to a second embodiment.

As shown in FIG. 21, a sensor system 210 according to the embodiment includes the sensor (e.g., the sensor 110) according to the first embodiment and other sensors. Other sensors include at least one of a capacitive gas sensor 141 (for example, capacitive hydrogen sensor), a capacitive humidity sensor 142, a temperature sensor 143, a gas flow sensor 144, or a contact combustion type sensor 145. The sensor (e.g., sensor 110) according to the first embodiment includes, for example, a thermal conductivity gas sensor and a pressure sensor.

Various types of sensors are provided in the sensor system 210. A highly accurate and convenient sensor system can be provided. In the embodiment, the detection result of one sensor of a different type may be used to correct the detection results of one or more other sensor.

Figure 22:
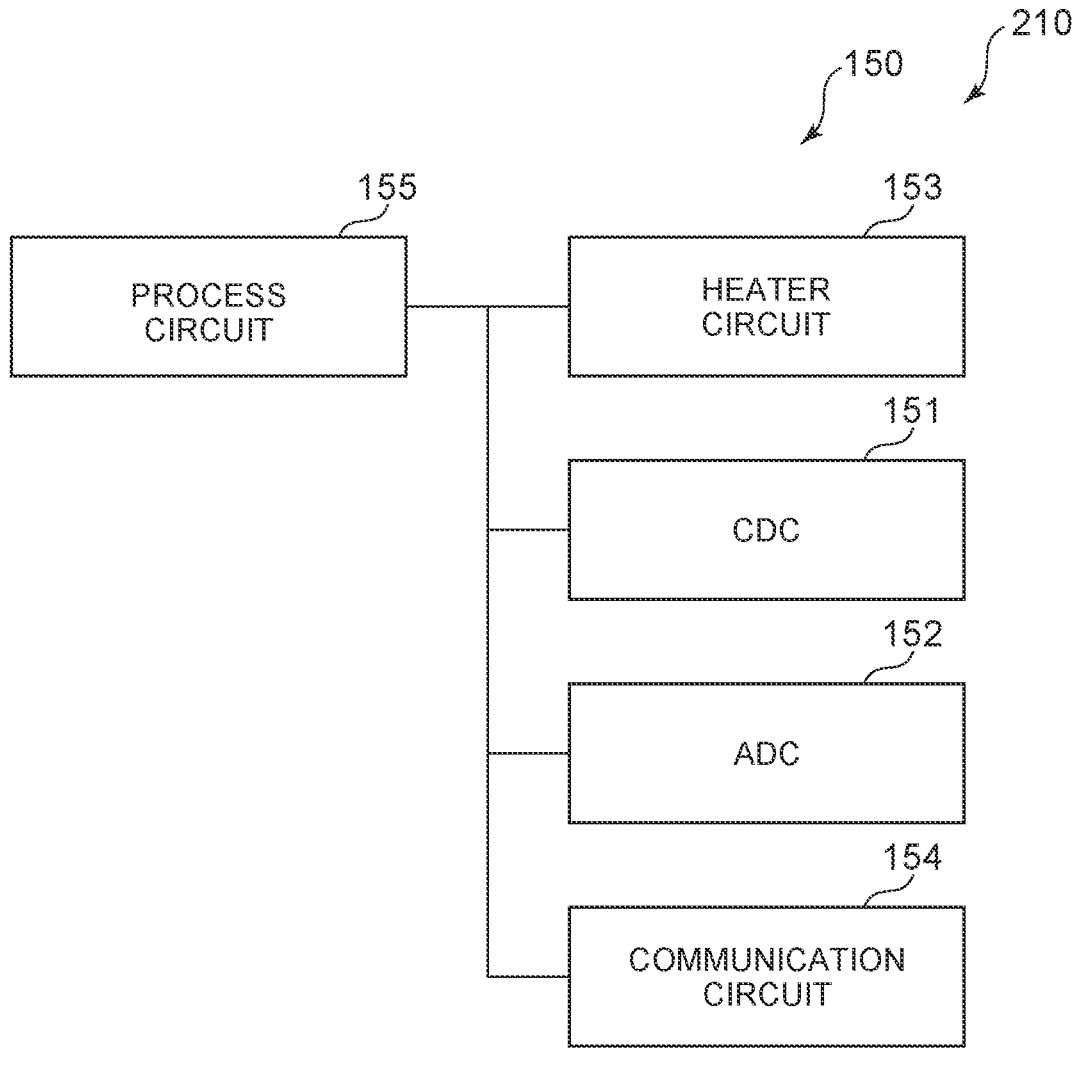
FIG. 22 is a circuit block diagram illustrating the sensor system according to the second embodiment.

FIG. 22 is a circuit block diagram illustrating the sensor system according to the second embodiment.

As shown in FIG. 22, the sensor system 210 may further include a circuit section 150. The circuit section 150 includes at least one of a CDC (Capacitance-to-Digital Converter) 151, an ADC (Analog-to-Digital Converter) 152, or a heater current supply circuit 153. The circuit section 150 may include a communication circuit 154. The circuit section 150 may include a processing circuit 155.

For example, the CDC 151 is configured to process the detection results of at least one of the capacitive gas sensor 141, the capacitive humidity sensor 142 or the sensor 110.

The ADC 152 is configured to process the detection result of at least one of the temperature sensor 143, the gas flow sensor 144, the contact combustion type sensor 145 or the sensor 110.

The heater current supply circuit 153 is configured to supply current to the first conductive member 31$c$ of the sensor 110, for example. At least one of the sensor 110, the capacitive gas sensor 141, the gas flow sensor 144, and the contact combustion type sensor 145 is driven by the heater current supply circuit 153, for example.

The processing circuit 155 may process the processing results of the CDC 151 and the ADC 152. The processing circuit 155 may be configured to control the CDC 151, the ADC 152 and the heater current supply circuit 153. The communication circuit 154 is configured to transmit the detection results.

The embodiments may include the following configurations (for example, technical proposals).

Configuration 1

A sensor, comprising:
a base including a first region and a second region; and
a first sensor section,
the first sensor section including
    a first support portion fixed to the first region,
    a first structure supported by the first support portion,
    the first structure including a first resistance member,
    a first direction from the second region to the first structure crossing a second direction from the first region to the second region, and
    a first film portion fixed to the first region, a first gap being provided between the second region and the first film portion, a second gap being provided between the first film portion and the first structure.

Configuration 2

The sensor according to Configuration 1, wherein
a first pressure in a first space between the second region and the first film portion is lower than a second pressure in a second space between the first film portion and the first structure.

Configuration 3

The sensor according to Configuration 2, wherein
a first film portion distance between the second region and the first film portion is variable according to a pressure in the second space.

Configuration 4

The sensor according to Configuration 3, wherein
a first structure distance between the second region and the first structure does not change, or
a change in the first structure distance is smaller than a change in the first film portion distance

Configuration 5

The sensor according to Configuration 3, wherein
a pressure in the second space in a first state is higher than a pressure in the second space in a second state,
the first film portion distance in the first state is shorter than the first film portion distance in the second state, and
a distance between the first film portion and the first structure in the first state is longer than a distance between the first film portion and the first structure in the second state.

Configuration 6

The sensor according to Configuration 2, wherein
the first space is sealed by the second region and the first film portion.

Configuration 7

The sensor according to Configuration 6, wherein
the first sensor section further includes a first intermediate film,
the first intermediate film is provided between the second region and the first film portion, and is fixed to the first film portion,
the first intermediate film includes a first hole piercing the first intermediate film in the first direction, and
the first gap is provided between the second region and the first intermediate film.

Configuration 8

The sensor according to Configuration 3, further comprising:
a controller,
the first structure further including a first conductive member, the controller being configured to increase a temperature of the first structure by supplying power to the first conductive member, and the controller being configured to detect a change in a first electrical resistance of the first resistance member according to a change in the temperature of the first structure.

Configuration 9

The sensor according to Configuration 8, wherein
the first electrical resistance changes according to a detection target gas around the first structure.

Configuration 10

The sensor according to Configuration 9, wherein
a pressure in the second space in a first state is higher than a pressure in the second space in a second state,
the first film portion distance in the first state is shorter than the first film portion distance in the second state,
a distance between the first film portion and the first structure in the first state is longer than the distance between the first film portion and the first structure in the second state, and
conduction of heat of the first structure to the first film portion decreases as the distance between the first film portion and the first structure increases.

Configuration 11

The sensor according to Configuration 9, wherein
the controller is configured to detect a change in electrical capacitance between the base and the first film portion, and
the controller is configured to correct a detection result of a change in the first electrical resistance based on the detection result of a change in the electrical capacitance.

Configuration 12

The sensor according to Configuration 11, wherein
the first film portion is conductive, and
at least a part of the second region is conductive.

Configuration 13

The sensor according to Configuration 11, wherein
the first film portion includes polysilicon, and
the base includes silicon.

Configuration 14

The sensor according to Configuration 13, wherein
the first structure includes a first insulating member,
at least a part of the first insulating member is provided around the first resistance member, and
the first insulating member includes silicon and nitrogen.

Configuration 15

The sensor according to any one of Configurations 1-14, wherein
the first sensor section further includes a first connect portion, a part of the first connect portion is connected to the first support portion,
another part of the first connect part is connected to the first structure,
a width of the first connect portion in a third direction is narrower than a width of the first structure in the third direction, and
the third direction crosses a plane including the first direction and the second direction.

Configuration 16

The sensor according to any one of Configurations 1-15, wherein
the first support portion includes a first support part and a second support part,
the first support part is fixed to the first region,
the second support part is continuous with the first support part,
the first sensor section further includes a first fixing member,
the first fixing member is provided between a part of the first film portion and the second support part, and is fixed to the first film portion, and
a third gap is provided between the first fixing member and the second support part.

Configuration 17

The sensor according to Configuration 8, further comprising:
a second sensor section,
the second sensor section includes
a second support portion fixed to the third region, and
a second structure including a second resistance member, the second structure being supported by the second support portion, a direction from the fourth region to the second structure being along the first direction, and
a fourth gap being provided between the fourth region and the second structure.

Configuration 18

The sensor according to Configuration 17, wherein
the controller is configured to correct a detection result of the change in the first electrical resistance based on a detection result of a second electrical resistance of the second resistance member.

Configuration 19

A sensor system, comprising:
the sensor according to any one of Configurations 1-18; and
another sensor,
the other sensor including at least one of a capacitive gas sensor, a capacitive humidity sensor, a temperature sensor, a gas flow sensor, or a contact combustion type sensor.

Configuration 20

The sensor system according to Configuration 19, further comprising:

a circuit section, the circuit section including at least one of a CDC (Capacitance-to-Digital Converter), an ADC (Analog-to-Digital Converter), or a heater current supply circuit, the CDC is configured to process a detection result of at least one of the sensor, the capacitive gas sensor, and the capacitive humidity sensor, and the ADC is configured to process a detection result of at least one of the sensor, the temperature sensor, the gas flow sensor, or the contact combustion type sensor.

According to the embodiments, a sensor and a sensor system capable of improving accuracy can be provided.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as bases, sensor sections, support portions, structures, film portions, controllers, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors and all sensor systems practicable by an appropriate design modification by one skilled in the art based on the sensors and the sensor systems described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:

a base including a first region and a second region; and a first sensor section, the first sensor section including a first support portion fixed to the first region, a first structure supported by the first support portion, the first structure including a first resistance member, a first direction from the second region to the first structure crossing a second direction from the first region to the second region, and a first film portion fixed to the first region, a first gap being provided between the second region and the first film portion, a second gap being provided between the first film portion and the first structure, wherein a first pressure in a first space between the second region and the first film portion is lower than a second pressure in a second space between the first film portion and the first structure, the first space is sealed by the second region and the first film portion, the first sensor section further includes a first intermediate film, the first intermediate film is provided between the second region and the first film portion, and is fixed to the first film portion, the first intermediate film includes a first hole piercing the first intermediate film in the first direction, and the first gap is provided between the second region and the first intermediate film.

2. The sensor according to claim 1, wherein a first film portion distance between the second region and the first film portion is variable according to a pressure in the second space.

3. The sensor according to claim 2, wherein a first structure distance between the second region and the first structure does not change, or a change in the first structure distance is smaller than a change in the first film portion distance.

4. The sensor according to claim 2, wherein a pressure in the second space in a first state is higher than a pressure in the second space in a second state, the first film portion distance in the first state is shorter than the first film portion distance in the second state, and a distance between the first film portion and the first structure in the first state is longer than a distance between the first film portion and the first structure in the second state.

5. The sensor according to claim 1, wherein the first sensor section further includes a first connect portion, a part of the first connect portion is connected to the first support portion, another part of the first connect part is connected to the first structure, a width of the first connect portion in a third direction is narrower than a width of the first structure in the third direction, and the third direction crosses a plane including the first direction and the second direction.

6. The sensor according to claim 1, wherein the first support portion includes a first support part and a second support part, the first support part is fixed to the first region, the second support part is continuous with the first support part, the first sensor section further includes a first fixing member, the first fixing member is provided between a part of the first film portion and the second support part, and is fixed to the first film portion, and a third gap is provided between the first fixing member and the second support part.

7. A sensor system, comprising:

the sensor according to claim 1; and another sensor, the other sensor including at least one of a capacitive gas sensor, a capacitive humidity sensor, a temperature sensor, a gas flow sensor, or a contact combustion type sensor.

8. The sensor system according to claim 7, further comprising:

a circuit section, the circuit section including at least one of a CDC (Capacitance-to-Digital Converter), an ADC (Analog-to-Digital Converter), or a heater current supply circuit, the CDC is configured to process a detection result of at least one of the sensor, the capacitive gas sensor, and the capacitive humidity sensor, and the ADC is configured to process a detection result of at least one of the sensor, the temperature sensor, the gas flow sensor, or the contact combustion type sensor.

9. A sensor, comprising:

a base including a first region and a second region;

a first sensor section; and a controller, the first sensor section including a first support portion fixed to the first region, a first structure supported by the first support portion, the first structure including a first resistance member, a first direction from the second region to the first structure crossing a second direction from the first region to the second region, and a first film portion fixed to the first region, a first gap being provided between the second region and the first film portion, a second gap being provided between the first film portion and the first structure, a first pressure in a first space between the second region and the first film portion being lower than a second pressure in a second space between the first film portion and the first structure, a first film portion distance between the second region and the first film portion being variable according to a pressure in the second space, the first structure further including a first conductive member, the controller being configured to increase a temperature of the first structure by supplying power to the first conductive member, and the controller being configured to detect a change in a first electrical resistance of the first resistance member according to a change in the temperature of the first structure.

10. The sensor according to claim 9, wherein the first electrical resistance changes according to a detection target gas around the first structure.

11. The sensor according to claim 10, wherein a pressure in the second space in a first state is higher than a pressure in the second space in a second state, the first film portion distance in the first state is shorter than the first film portion distance in the second state, a distance between the first film portion and the first structure in the first state is longer than the distance between the first film portion and the first structure in the second state, and conduction of heat of the first structure to the first film portion decreases as the distance between the first film portion and the first structure increases.

12. The sensor according to claim 10, wherein the controller is configured to detect a change in electrical capacitance between the base and the first film portion, and the controller is configured to correct a detection result of a change in the first electrical resistance based on the detection result of a change in the electrical capacitance.

13. The sensor according to claim 12, wherein the first film portion is conductive, and at least a part of the second region is conductive.

14. The sensor according to claim 12, wherein the first film portion includes polysilicon, and the base includes silicon.

15. The sensor according to claim 14, wherein the first structure includes a first insulating member, at least a part of the first insulating member is provided around the first resistance member, and the first insulating member includes silicon and nitrogen.

16. The sensor according to claim 9, further comprising:

a second sensor section, the base further includes a third region and a fourth region, the second sensor section includes a second support portion fixed to a third region, and a second structure including a second resistance member, the second structure being supported by the second support portion, a direction from the fourth region to the second structure being along the first direction, and a fourth gap being provided between the fourth region and the second structure.

17. The sensor according to claim 16, wherein the controller is configured to correct a detection result of the change in the first electrical resistance based on a detection result of a second electrical resistance of the second resistance member.

18. A sensor, comprising:

a base including a first region and a second region;

a first sensor section; and a controller, the first sensor section including a first support portion fixed to the first region, a first structure supported by the first support portion, the first structure including a first resistance member, a first direction from the second region to the first structure crossing a second direction from the first region to the second region, and a first film portion fixed to the first region, a first gap being provided between the second region and the first film portion, a second gap being provided between the first film portion and the first structure, the first structure further including a first conductive member, the controller being configured to increase a temperature of the first structure by supplying power to the first conductive member, and the controller being configured to detect a change in a first electrical resistance of the first resistance member according to a change in the temperature of the first structure.

* * * * *